(12) United States Patent
Dirani et al.

(10) Patent No.: US 11,373,740 B2
(45) Date of Patent: Jun. 28, 2022

(54) APPARATUS AND METHOD FOR MONITORING USE OF A DEVICE

(71) Applicants: SINGAPORE HEALTH SERVICES PTE LTD, Singapore (SG); Mohamed Dirani, Melbourne (AU)

(72) Inventors: Mohamed Dirani, Melbourne (AU); Tien Yin Wong, Singapore (SG); Dan Belkin, Singapore (SG); Xiaoqin Fang, Singapore (SG)

(73) Assignee: PLANO PTE LTD, Singapore (SG)

( * ) Notice: Subject to any disclaimer, the term of this patent is extended or adjusted under 35 U.S.C. 154(b) by 263 days.

(21) Appl. No.: 16/315,162

(22) PCT Filed: Jun. 15, 2017

(86) PCT No.: PCT/SG2017/050305
§ 371 (c)(1),
(2) Date: Jan. 4, 2019

(87) PCT Pub. No.: WO2018/009144
PCT Pub. Date: Jan. 11, 2018

(65) Prior Publication Data
US 2019/0252054 A1    Aug. 15, 2019

(30) Foreign Application Priority Data

Jul. 4, 2016   (SG) ............... 10201605461U

(51) Int. Cl.
*G16H 20/00*     (2018.01)
*G16H 20/30*     (2018.01)
(Continued)

(52) U.S. Cl.
CPC ............. *G16H 20/00* (2018.01); *G06F 9/451* (2018.02); *G06F 9/453* (2018.02); *G16H 20/30* (2018.01);
(Continued)

(58) Field of Classification Search
CPC ........ G06F 3/012; G06F 3/013; G06F 3/0484; G06F 9/453; G06F 9/451; G06F 8/61;
(Continued)

(56) References Cited

U.S. PATENT DOCUMENTS 10,440,499 B2* 10/2019 Farrell .................... H04W 4/02
2013/0139082 A1* 5/2013 Wheeler ................. G06F 3/012
715/765

(Continued)

FOREIGN PATENT DOCUMENTS

CN      1703915 A       11/2005
CN      1917564 A  *    2/2007
(Continued)

*Primary Examiner* — Steven P Sax
(74) *Attorney, Agent, or Firm* — Soroker Agmon Nordman Pte Ltd

(57) ABSTRACT

A method and apparatus for monitoring arid for improving eye health of a user of a device, the method comprising receiving m indication that an event occurred associated with rise of the device; updating data on the device according to the data included in a user profile associated with a user; generating a personalized user interface and displaying said interface on the device; detecting a distance of the user from the device; and providing an indication once the distance exceeds a predefined threshold for a predefined time period.

15 Claims, 12 Drawing Sheets

(51) Int. Cl.
*G16H 40/63* (2018.01)
*G16H 50/30* (2018.01)
*G06F 9/451* (2018.01)
*G06F 8/61* (2018.01)

(52) U.S. Cl.
CPC .............. *G16H 40/63* (2018.01); *G16H 50/30* (2018.01); *G06F 8/61* (2013.01)

(58) Field of Classification Search
CPC ........... G02B 27/0101; H04N 1/00129; H04N 2201/0089; B60J 3/02; G16H 20/00; G16H 20/30; G16H 40/63; G16H 50/30
See application file for complete search history.

(56) References Cited

U.S. PATENT DOCUMENTS

| | | | | |
|---|---|---|---|---|
| 2013/0281014 | A1* | 10/2013 | Frankland | H04W 4/80 455/41.1 |
| 2014/0028458 | A1 | 1/2014 | Shin et al. | |
| 2014/0041042 | A1* | 2/2014 | Wong | G06F 21/6245 726/26 |
| 2014/0118354 | A1* | 5/2014 | Pais | G09G 5/373 345/428 |
| 2014/0129259 | A1* | 5/2014 | Seriani | G16H 80/00 705/3 |
| 2014/0137054 | A1* | 5/2014 | Gandhi | G06F 3/0484 715/865 |
| 2014/0285429 | A1* | 9/2014 | Simmons | H04N 1/00129 345/156 |
| 2014/0285436 | A1* | 9/2014 | Wu | A61B 5/1116 345/156 |
| 2014/0350727 | A1* | 11/2014 | Desai | H04N 5/23206 700/259 |
| 2015/0091824 | A1* | 4/2015 | Hori | G06F 3/04883 345/173 |
| 2015/0190048 | A1* | 7/2015 | Huang | A61B 3/0033 351/239 |
| 2016/0026241 | A1 | 1/2016 | Leung | |
| 2016/0250554 | A1* | 9/2016 | Haigh-Hutchinson | A63F 13/04 463/32 |
| 2016/0262608 | A1* | 9/2016 | Krueger | G06T 19/006 |
| 2016/0299360 | A1* | 10/2016 | Fonte | G02C 13/005 |
| 2016/0309998 | A1* | 10/2016 | Gonzalez Garcia | A61B 3/14 |
| 2016/0314729 | A1* | 10/2016 | Gutierrez | G09G 3/003 |
| 2016/0357014 | A1* | 12/2016 | Beckman | B60J 3/04 |
| 2017/0160798 | A1* | 6/2017 | Lanman | G02B 27/0172 |
| 2017/0294175 | A1* | 10/2017 | Chen | G09G 5/10 |

FOREIGN PATENT DOCUMENTS

| | | | | |
|---|---|---|---|---|
| CN | 202179524 U | * | 4/2012 | |
| CN | 202679497 U | | 1/2013 | |
| CN | 103369274 A | | 10/2013 | |
| CN | 103700229 A | | 4/2014 | |
| CN | 103873667 A | | 6/2014 | |
| CN | 204069033 U | | 12/2014 | |
| CN | 104407963 A | | 3/2015 | |
| CN | 104427275 A | | 3/2015 | |
| CN | 204501127 U | | 7/2015 | |
| CN | 105278692 A | | 1/2016 | |
| CN | 105282300 A | | 1/2016 | |
| CN | 105468147 A | | 4/2016 | |
| JP | I289437 B | * | 11/2007 | |
| JP | 2010182287 A | * | 8/2010 | |
| WO | WO-2008151346 A1 | * | 12/2008 | ............ A61B 3/113 |
| WO | 2015191183 A2 | | 12/2015 | |

* cited by examiner

APPARATUS AND METHOD FOR MONITORING USE OF A DEVICE

FIELD OF THE INVENTION

The present disclosure generally relates to the field of monitoring the use of smart devices, and more specifically to the use of a smart device applications for the monitor and improvement of general health and more specifically eye health or for preventing deterioration in general health with the emphasis on eye health (myopia).

BACKGROUND

The distribution of the myopia disorder, also known as near sightedness or short sightedness, has increased dramatically over the past few years in the general population, and more specifically, in children. This phenomenon is significantly higher among the Asian population compared to those of the Western population.

One of the reasons associated with the increase in myopia cases is the longer exposure time to screens, such as of smartphones and tablets, on a daily basis. Furthermore, the rise in myopia cases is associated with high public health and economic costs. Additionally, severe myopia cases may cause pathological eye changes that can lead to blindness.

Studies have shown that children, suffering from myopia face higher risks of developing eye problems later in life. In addition, in some Asian countries, the prevalence of myopia in children aged 11 through 18 had reached 69 percent, and children aged 7-9 were identified as having a significantly high prevalence of myopia. These indicate that myopia, especially in children, would become a significant public health issue. Therefore, the prevention and treatment of myopia is of significant concern and importance.

Furthermore, an excessive use of smart devices may also lead to an increased sedentary behavior, resulting in the reduction of outdoor and physical activity, less engagement with other people and/or sleep disorder.

SUMMARY

According to an aspect of some embodiments of the present invention there is provided a method for monitoring and for improving eye health of a user of a device, the method comprising receiving an indication that an event occurred associated with use of the device, updating data on the device according to the data included in a user profile associated with a user, generating a personalized user interface and displaying said interface on the device, detecting a distance of the user from the device; and providing an indication once the distance exceeds a predefined threshold for a predefined time period.

Optionally, the method further comprising detecting a face of the user and monitoring the distance between the user's face and the device.

Optionally, the method further comprising detecting an eye of the user and monitoring the distance between the user's eye and the device.

Optionally, the method further comprising detecting glasses of the user and monitoring the distance between the user's glasses and the device.

Optionally, the method further comprising detecting the location of the device and monitoring the distance between the user's face and the device or the duration of the use of the device, based on the location of the device.

Optionally, the method further comprising detecting the ambient light around the device and monitoring the distance between the user's face and the device or the duration of the use of the device, based on the amount of light surrounding the device.

Optionally, the method further comprising receiving data from the device of a managing user.

Optionally, the method further comprising creating the managing user profile including data regarding at least one user.

Optionally, the method further comprising generating a varying user interface, providing the user the effect of focusing on objects located in a variety of different distances.

Optionally, the method further comprising generating a varying user interface upon failure of the user to comply with the indication, providing the user the effect of focusing on objects located in a variety of different distances.

Optionally, the method further comprising generating according to received data from the device or from other devices alerts about one from a group consisting of the user's eyes condition, the user's use of the device, the ambient light surrounding the device, the location of the device and the progression of myopic condition of the user of the device.

Optionally, the method further comprising providing the user of the device an incentive if the indication is complied with.

Optionally, the method further comprising receiving from the device data about detected ambient light, and instructing the device to apply a blue light filter once the ambient light/screen light differential meets a pre-determined threshold.

Optionally, the method further comprising receiving from the device data about detected orientation of the device and instructing the device to notify the user when the holding position exceeds a predetermined threshold.

Optionally, the method further comprising adjusting the predetermined distance based on the data received from the sensors.

Optionally, the method further comprising adjusting the predetermined time session based on the data received from the sensors. Optionally, the method further comprising presenting to the user an image that allows the user to focus his eyes on a focal point distant from the actual focal point of a display of the device.

According to an aspect of some embodiments of the present invention there is provided an apparatus for monitoring the eye health of a user, the apparatus comprising: a device having a memory storing code instructions, a hardware processor and a display, the hardware processor is configured to execute code instructions for: receiving indication that an event occurred that is associated with use of the device, updating data on the device according to the data included in a user profile associated with a user of the device, generating a personalized user interface and displaying on the display of the device, detecting a distance of the user from the device and providing an indication once the distance between the user and the device exceeds a predefined threshold for a predefined time period.

According to another aspect of some embodiments of the present invention there is provided a method including:

BRIEF DESCRIPTION OF THE DRAWINGS

Some non-limiting exemplary embodiments or features of the disclosed subject matter are illustrated in the following drawings.

In the drawings.

Figure 1:
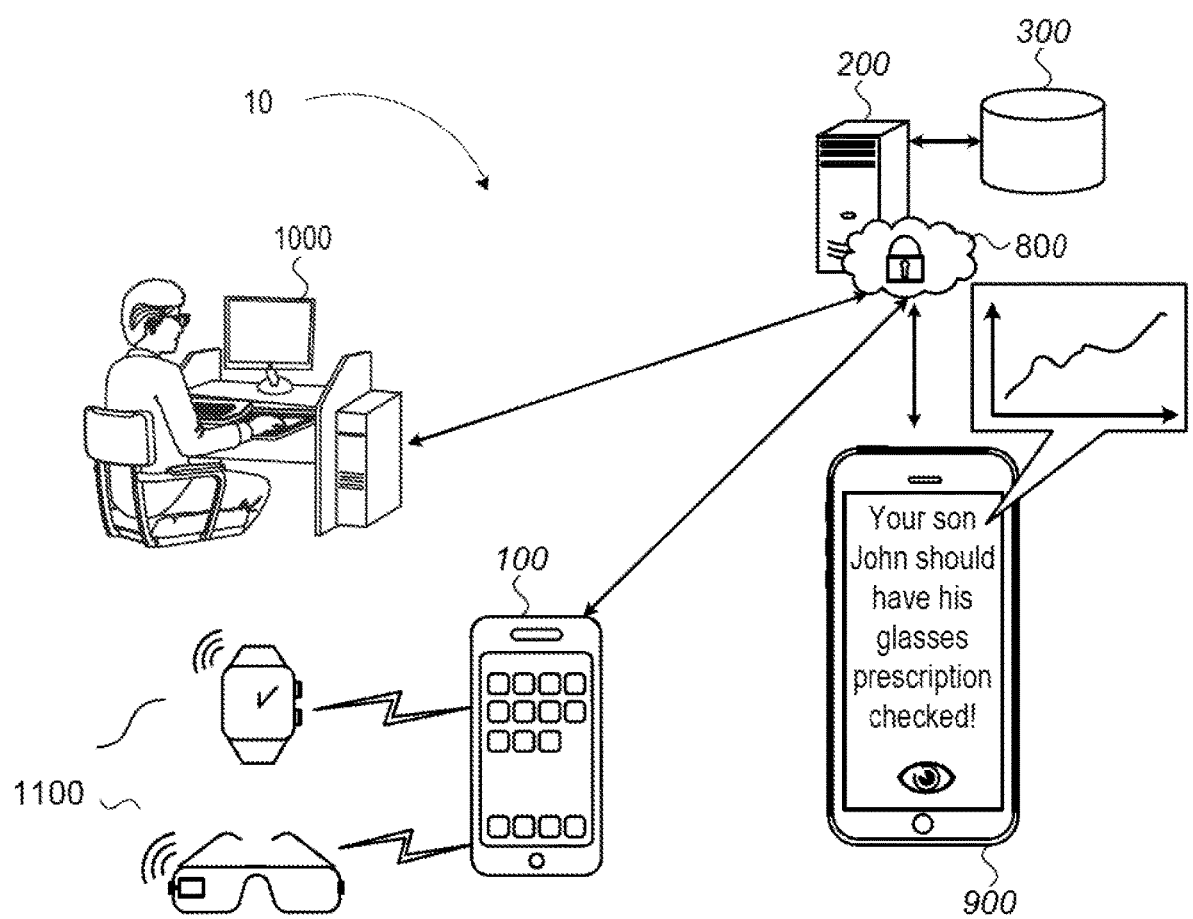
FIG. 1 is a schematic illustration of a system for eye health monitoring, according to some embodiments of the present invention.

With specific reference now to the drawings in detail, it is stressed that the particulars shown are by way of example and for purposes of illustrative discussion of some embodiments of the invention. In this regard, the description taken with the drawings makes apparent to those skilled in the art how embodiments of the invention may be practiced.

Identical or duplicate or equivalent or similar structures, elements, or parts that appear in one or more drawings are generally labeled with the same reference numeral, optionally with an additional letter or letters to distinguish between similar entities or variants of entities, and may not be repeatedly labeled and/or described. References to previously presented elements are implied without necessarily further citing the drawing or description in which they appear.

Dimensions of components and features shown in the figures are chosen for convenience or clarity of presentation and are not necessarily shown to scale or true perspective. For convenience or clarity, some elements or structures are not shown or shown only partially and/or with different perspective or from different point of views.

DETAILED DESCRIPTION

Some embodiments of the present invention provide a tool for dealing with the growing myopia prevalence. According to research, the myopia disorder is rising in children worldwide in general and with the Asian population in particular. Changes in lifestyle in the past decade, such as use of smart phones and tablets on a daily basis and lack of outdoor activity, are considered as parameters affecting the increase in myopia.

While some known systems are capable of establishing the distance of a user to the PC or laptop screen, the currently known systems do not provide any solution for the use of the smart phones or tablets or other screen related devices such as smart watches, which are devices that are used on a daily basis, for reducing the prevalence of myopia through the monitoring of use and changing the behavior of children using such devices.

As opposed to known methods, the provided tool enables scalable interventions to reduce or prevent the onset of myopia, for example by providing reminders and/or notifications during everyday use of smart devices. For example, the tool may provide reminders to perform simple exercises such as looking away from the screen for a few minutes every once in a while.

Some embodiments of the present invention provide for supervisors, for example parents, with an easily accessible tool helping to reduce, halt progression of and/or prevent myopia in a child or in another supervised person. Therefore, a technological solution is provided, that focuses on addressing the problem of myopia. For example, some embodiments provide a supervisor with an eye health focused tool to manage and/or monitor use of smart devices by a supervised person. This tool also monitors, detects and manages how children use their devices to ensure devices are held at an appropriate distance from the user's eyes, to ensure safe screen illuminations for night use and encourage outdoor activity.

Throughout the present description, the term "supervised person" or "supervisee" means a child, an old parent, a patient, a disabled person, and/or any other suitable supervised person. Similarly, the term "supervisor" means a parent, a guardian, a custodian, a therapist, a physician, a caregiver, and/or any other suitable supervisor.

Furthermore, the solution provides a supervisor with an ongoing real-time live data regarding device use habits, device holding positions, outdoor activity, and/or eye condition of a supervisee, thus facilitating better personalization of device use management. For example, the provided tool enables the supervisor to view and monitor in real time eye health data and device use data of a supervised person.

The solution described herein enables supervisors to download to smart devices a software application focused on addressing various ocular problems with an emphasis on myopia and addressing the problems in an effective way through gamification, feedback and incentives that encourage supervised children and/or other supervisees to change their behavior by adapting safer use habits when using their devices.

Some embodiments of the present invention may include a system, a method, and/or a computer program product The computer program product may include a tangible non-transitory computer readable storage medium (or media) having computer readable program instructions thereon for causing a processor to carry out aspects of the present invention. Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including any object oriented programming language and/or conventional procedural programming languages.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a schematic illustration of a system 10 for eye health monitoring, according to some embodiments of the present invention. System 10 may include a user device 100, a server 200, a database 300 and/or a supervising device 900. Device 100 and/or server 200 may communicate with each other and/or with other devices via a public and/or private network 800. Such network 800 may be a wide area network and may include cellular, landline, wireless, Bluetooth and/or any other suitable sort of network technology. In some embodiments, as described in detail herein, system 10 may include at least one wearable device 1100.

Device 100 may be connected to and/or communicate with a server 200, a database 300 and/or a supervising device 900 through network 800. Supervising device 900 may be used by a supervisor to supervise use of device 100 by a supervised user. It should be noted that user device 100 may include smart phones, tablets, a PC, a laptop or other screen related devices such as smart watches. For example, user device 100 includes smart watch 1100 as shown in FIG. 1. It should be noted that the supervising device 900 may include a desktop computer, a laptop, a tablet, a smart phone and/or any other suitable computerized device. For example, supervising device 900 includes PC 1000 as shown in FIG. 1. The user's device 100 may communicate with a smartwatch, smart glasses and/or other wearable device 1100. Communication between user device 100. supervisor's device 900, wearable device 1100, server 200 and/or database 300 may be made by Bluetooth, cellular network, landline and/or wireless network, or by any other suitable network connection, for example via network 800 and/or another network.

In some embodiment of the present invention, device 100 may collect and/or process information about characteristics of use of device 100, as described in more detail herein. At least some of the collected and/or processed information may be transmitted to server 200, which may store the information as user data in database 300, with relation to the respective user.

Device 100 may download from server 200 and/or an application store, and/or install on device 100, a software application for supervised use, of device 100, supervised and/or controlled by supervising device 900 and/or server 200.

A supervisor may download to and/or install on device 900, from server 200 and/or an application store, a software application for supervising use of device 100 by communication with server 200. In some embodiments of the present invention, a supervisor may provide to server 200, for example by entering to the downloaded supervising application, information about a user of device 100, and server 200 may store the information in database 300 with relation to the respective user. The provided data may include user's eye prescription, user's age, predetermined time periods and/or working distance. Processor 102 may receive relevant information from server 200, and decide based on the information about parameters and/or conditions for generation of notifications, alerts, and/or other actions. Processor 102 may request and/or receive information stored on database 300 from server 200. In some embodiments, processor 102 may store at least some of the received information in memory 114, making it available for use on device 100 even without connection to network 800 and/or server 200.

Based on use information collected and/or processed by device 100, processor 102 may generate notifications to a user of device 100, for example informing the user of an action that should be taken. For example, processor 102 may inform the user to keep a certain distance from a screen, to take a break from using a device, to change setting of a device, and/or any other suitable notification. In some embodiments, processor 102 may generate a notification to a supervisor and/or transmit a notification request to server 200. Upon receiving the notification request, server 200 may transmit a corresponding notification to supervising device 900. Server 200 may store the notifications and/or data about notifications in database 300 with relation to the corresponding user, for example in order to identify behavior patterns of the user. For example, server 200 may notify a supervisor in case a supervised user gets the same notification more than a predetermined number of times.

In some embodiments, a supervisor may send a request to server 200, for example via the supervising application, to change settings of the supervised use application installed on device 100 and/or settings of device 100. The data on database 300 may be updated by through device 100, device 900 and/or a professional or other persons, for example through the authorization of the supervisor.

Figure 2:
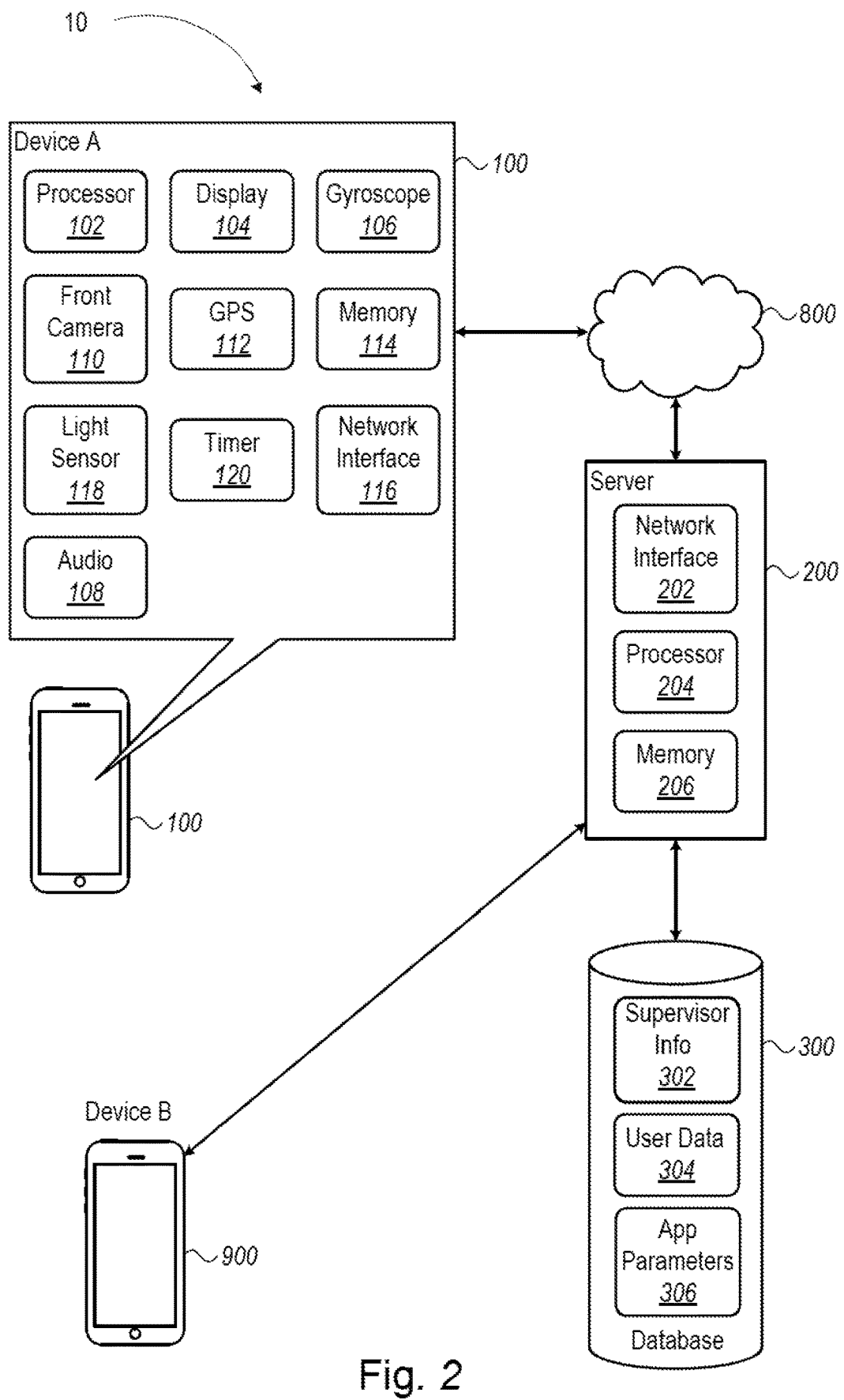
FIG. 2 is a schematic more detailed illustration of a system for eye health monitoring, according to some embodiments of the present invention.

Turning now to FIG. 2, which is a more detailed illustration of a system 10 for eye health monitoring, according to some embodiments of the present invention. In some embodiments, user device 100 includes at least one hardware processor 102, a display 104, a gyroscope 106, a front camera 110, a global positioning system (OPS) 112, a memory 114, a light sensor 118, a timer 120, a network interface 116 and an audio unit 108. Server 200 may include network interface 202, processor 204, and/or memory 206. Database 300 may include supervisor information 302, user data 304 and/or application parameters 306, as described in more detail herein. Although connections are not shown between the components illustrated in FIG. 2, the components can interact and/or communicate with each other to carry out methods described herein. It should be understood that FIG. 2 and the following description are intended to provide a general understanding of a suitable environment in which various aspects of embodiments can be implemented. User's device 100, supervisor's device 900, and/or device 1000 may be configured as user device 100. It should be understood that user device 100 may include additional functionality or include less functionality than now described.

Memory 114 may store code instructions executable by processor 102, for example causing processor 102 to carry out operations according to some embodiments of the present invention. Processor 102 may process data and/or execute computer-executable instructions stored in memory 114. Additionally, processor 102 ma extract data from and/or into memory 114 and/or database 300, thus, for example, making the data available for processing and/or analysis by processor 102.

Processor 102 may use camera 110 for monitoring a user's face, glasses, eye and/or pupil. During operation, for example while using device 100 by a supervised user, camera 110 may capture images of the user. Processor 102 may obtain the captured images and store in memory 114. Processor 102 may process the captured images obtained from camera 110. For example, processor 102 compares a chronological series of images captured by camera 102 and/or calculates, based on the series of images, the distance between the user and user device 100. The calculation may be done, for example, by comparing the ratio between the user's face and eye. For example, as the eye grows bigger (compared to the previous pictures), processor 102 may deduce that the user's face is getting closer to device 100. In some embodiments, the calculation may be done by comparing the ratio between the user's face and the entire frame/rest of the picture captured by camera 100. Furthermore, processor 102 may compare the user's stored pictures and detect when the user forgets to wear their glasses. In the present disclosure processor 102 may provide additional embodiments for example general face recognition capabilities, such as face, eyes, pupils and/or glasses recognition algorithms may be included.

Display 104 may visually display data including, but not limited to, graphical user interface ("GUI") elements, text, images, video, virtual keypads and/or keyboards, messaging data, notification messages, metadata, internet content, device status, time, map and location data, and/or any other suitable data. Display 104 may also provide the possibility of executing blue light filter display mode. For example, display 104 may adjust the lights and colors emitted for the screen depending on the light environments the device 100 is located therein.

Processor 102 may analyze position of device 100, for example based on orientation data received from gyroscope 106, and generate data for the user regarding the proper positioning of device 100. For example, processor 102 may generate a reminder letting the user know device 100 is not placed at the appropriate angle and to avoid positioning of device 100 in such a manner that may cause bad posture for the user.

Processor 102 may analyze location signals about the location of device 100, for example, signals received from GPS 112, and generate based on the analysis data for the user and/or a supervisor regarding the location of user device 100.

Processor 102 may analyze indications about illumination conditions in the surroundings of user device 100, for example indications received from light sensor 118. For example, based on the illumination conditions, processor 102 provides the supervisor with data regarding time spent in outdoor activities and/or change settings of display 104, such as activate/deactivate blue light filter display.

Processor 102 may track and analyze, using for example timer 120, the time spent by the user while using the device. This data may also enable processor 102 to analyze time sessions when device 100 is too close to the user or at the proper distance and send proper alerts.

In some embodiments, network interface 116 may facilitate communication by a cellular, wireless and or WI-FI or Bluetooth technology. Network interface 116 may enable processor 102 to communicate via network 800, for example with server 200, database 300 and/or supervisor's device 900.

Audio component 108 may include speaker for the output of audio signals and/or a microphone to collect audio signals. For example, audio 108 enables processor 102 to send audio alerts and collect audio data, as described in more detail herein below.

It should be understood that server 200 may include additional functionality or include less functionality than now described. Processor 204 may execute instructions stored on memory 206, causing processor 204 to carry out some embodiments of the present invention. Processor 204 may analyze, for example, images and data related to a user stored on database 300. Processor 204 may transmit data from database 300 to device 100 and/or device 900, for example upon request, and/or store on database 300 information received from device 100 and/or device 900. For example, processor 204 may receive images of a user from device 100 and compare them to previous images of the user stored in database 300. Based on the comparison, processor 204 may detect, for example, changes in the user's behavior. For example, processor 204 may detect that the user is not wearing glasses, that a typical distance of the user from the screen has changed, and/or any other relevant change in behavior. In case a change in behavior is detected, processor 204 may generate an alert to the supervisor's device 900.

It should be noted that the supervised use application installed on device 100 may prompt processor 102 to perform some of the described operations locally. Furthermore, server 200 may update the supervised use application and/or the supervising application from time to time, and install the updates in devices 100 and/or 900.

Accordingly, server 200 acts as an intermediate between device 100 and device 900, for example executing instructions received by device 900 and generating notifications for both devices. For example, as described in detail herein, processor 204 analyzes the data received from both devices, stores it on database 300 and/or generates proper notifications for device 900 and/or device 100.

In some embodiments, processor 204 generates rewards, incentive notifications and/or data regarding an incentive program. In some embodiments, processor 204 may generate and/or operate an incentive program, to motivate users to use device 100 in a proper way. For example, incentive points are rewarded to a user on proper use of device 100. In some embodiments, the rewards enable the unlocking of badges. These points can later be exchanged for vouchers, and the user can then decide which voucher to choose based on their personal preferences, as an e-commerce component of server 200. For example, once processor 204 detects that the data received from device 100 and/or stored on database 300 meets predetermined requirements, it may generate incentive points and notifications notifying a user and/or a corresponding supervisor, through device 100 and/or device 900, respectively, about the requirement that was met and/or about a received incentive.

It should be understood that database 300 may include additional functionality or include less functionality than now described. As described in more detail herein, database 300 stores the supervisor info 302, user data 304 and other related data, and/or it may also store via application parameters 306 a graphical user interface for example default font size. Supervisor info 302 may include, for example, the number and/or identity of supervisors and/or users, payment details, and/or user customizing preferences. The user data 304 may include, for example, personalized use restrictions and/or limitations, eye prescription, and/or incentive points.

Figure 3:
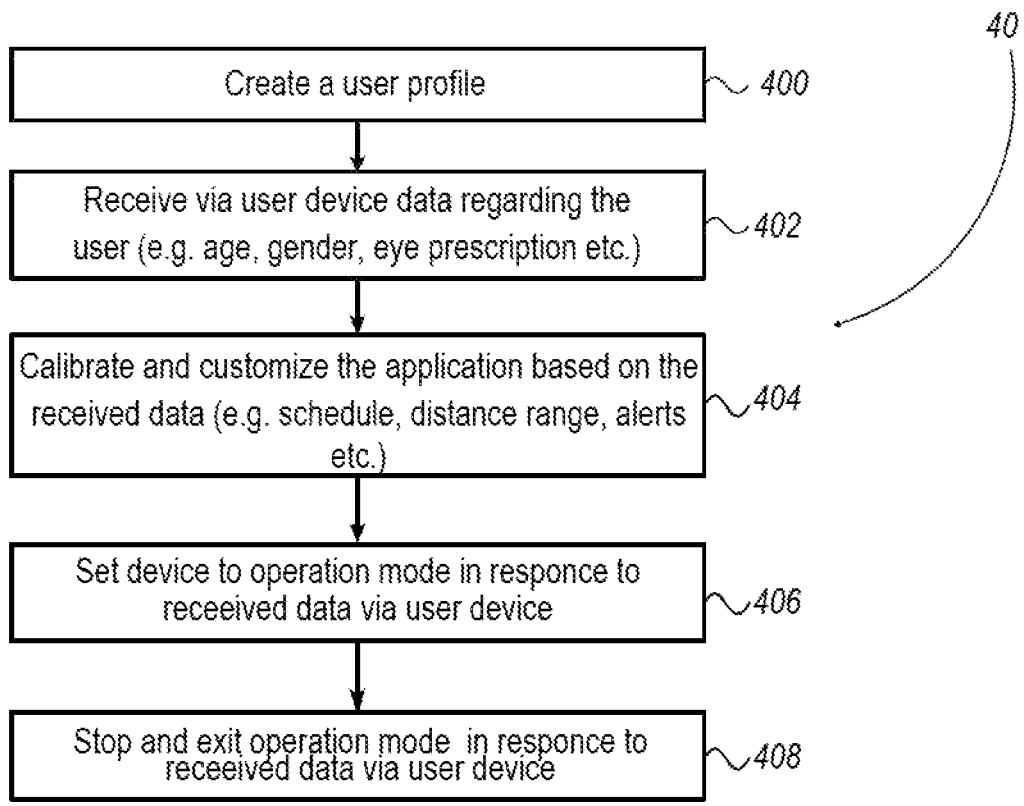
FIG. 3 is a schematic flowchart illustrating a method for eye-health monitoring, according to some embodiments of the present invention.

Turning to FIG. 3, which illustrates a method 40 for eye-health monitoring, according to some embodiments of the present invention, As indicated in block 400, processor 204 may create a user profile based on the information provided by the user and/or a corresponding supervisor, for example received via server 200. As indicated in block 402, processor 204 may obtain information entered by the user and/or a supervisor, and/or stored in database 300, may analyze the obtained information and/or may add the obtained information to the user profile. As indicated in block 404, processor 204 may extract the information entered by the supervisor and/or by a professional that is stored in database 300 and/or downloaded to memory 114, and customize the supervised use application accordingly.

Processor 204 may analyze the obtained information and/or store the analyzed information on database 300. For example, based on the analyzed information, processor 204 may customize configurations and/or functions of the supervised use application installed on device 100. For example, processor 204 may change alerts configuration and/or parameters on device 100 and/or the supervised use application, according to calibration details stored in database 300 In some embodiments, information stored in database 300 may be downloaded to device 100, stored, for example, in memory 114, and/or used by processor 102, for example, to perform operations instructed by the supervised use application. As indicated in block 406, and described in more detail, for example, in FIGS. 5A and 5B, processor 204 may receive collected information from device 100, such as images captured by camera 110 and/or other sensor data as described in detail herein.

In some embodiments, the supervised use application may enable a user and/or a supervisor to set device 100 to an operation mode, i.e. to start supervising the use of device 100 by processor 204 and/or by a supervisor device 900. For example, processor 204 may start receiving information from device 100 once the supervised use application is activated, i.e. device 100 is set to operation mode, and may process the information as described herein, for monitoring the user's behavior, for example as described herein with reference to FIG. 5A, block 500. As indicated in block 408, once the application is deactivated, processor 204 stops receiving information from device 100.

Figure 4A:
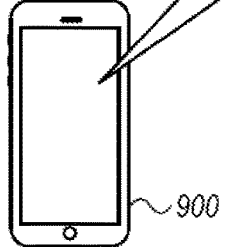
FIGS. 4A and 4B are a schematic illustration of an exemplary screen viewed on a supervisor's device when inserting data and customizing alerts, according to some embodiments of the present invention.

FIG. 4A is a schematic illustration of a screen 910 shown on supervisor's device 900 when the supervisor enters the user's information, as mentioned above, according to block 402 shown in FIG. 3. Processor 204 then extracts this data and analyzes it, for example to ensure that erroneous data is not entered into database 300. For example, in FIG. 4A the data entered represents that the left eve's prescription is higher than the right eye prescription. For example, processor 204 may generate a verity of alerts when analyzing the data and may detect that the user uses less or more of their right or left eye to view the screen. Such identification may be crucial to allow the device 100 to employ the methods described herein to assist in the correction of such behavior. The alerts generated by processor 204 may include, for example, a notification referring to an eye test to ensure that a refractive correction is up-to-date.

Figure 4B:
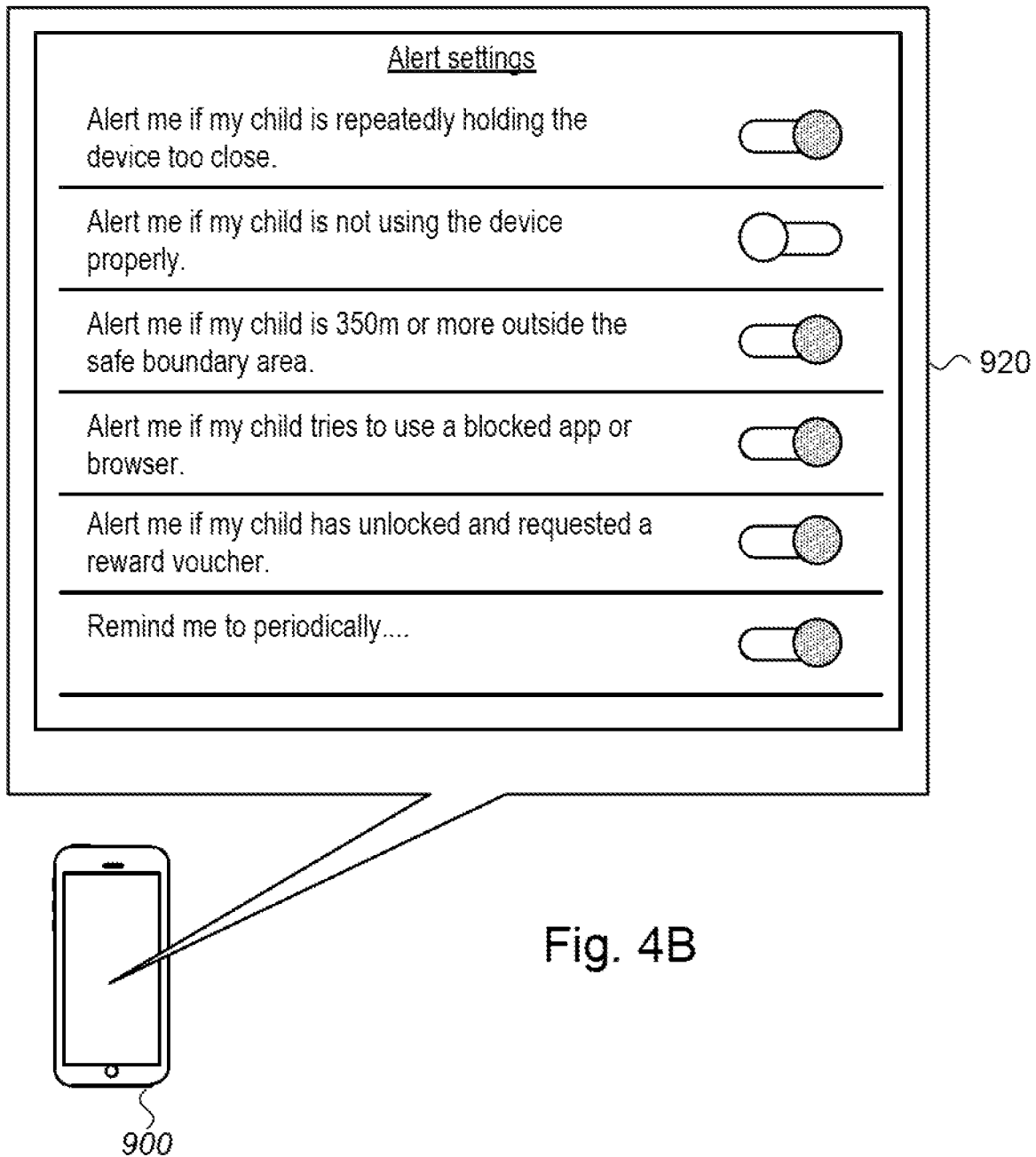

FIG. 4B is a schematic illustration of a screen 920 shown on supervisor's device 900 when customizing the preferences, according to block 404 shown in FIG. 3. For example, according to FIG. 4B processor 204 will provide an alert notification to the supervisor's device 900 when the user will repeatedly hold device 100 too close to their face. It should be noted that some of the calibrations, such as the working range, would need to be done by the supervisor and/or a professional, with or without the user, in order for processor 204 to be able to calculate the proper working distance. For example, processor 204 may receive from a supervisor and/or some professional calibration parameters, and calibrate the application accordingly, for example working ranges. For example, a supervisor and/or professional may enter that the recommended distance in which the device should be held away from the user is 30 cm. Then, when calibrating the application, processor 204 may add a tolerance (range) of, for example, 10 cm closer and 20 cm further. For example, processor 204 may calculate and analyze the series of images taken by camera 110 and stored in database 300 and/or memory 114, and determine that the working range should be in between 20 cm to 50 cm. It should also be noted that when customizing the application, the supervisor may set which notifications will be generated by processor 204 and sent to device 900 as well as device 100. It should be noted that when appropriate, method 40 is executed as a background application, i.e. once the supervisor and/or user selects operation mode as illustrated in block 406/410, method 50 is executed and the processor 204 continuously analyzes information provided thereto by the application of the device 100 embodying the methods of the present disclosure. Setting device 100 to an operation mode in connection with the methods of the present disclosure does not prevent the user from using other applications and/or functionality or from any other use of device 100.

Figure 5A:
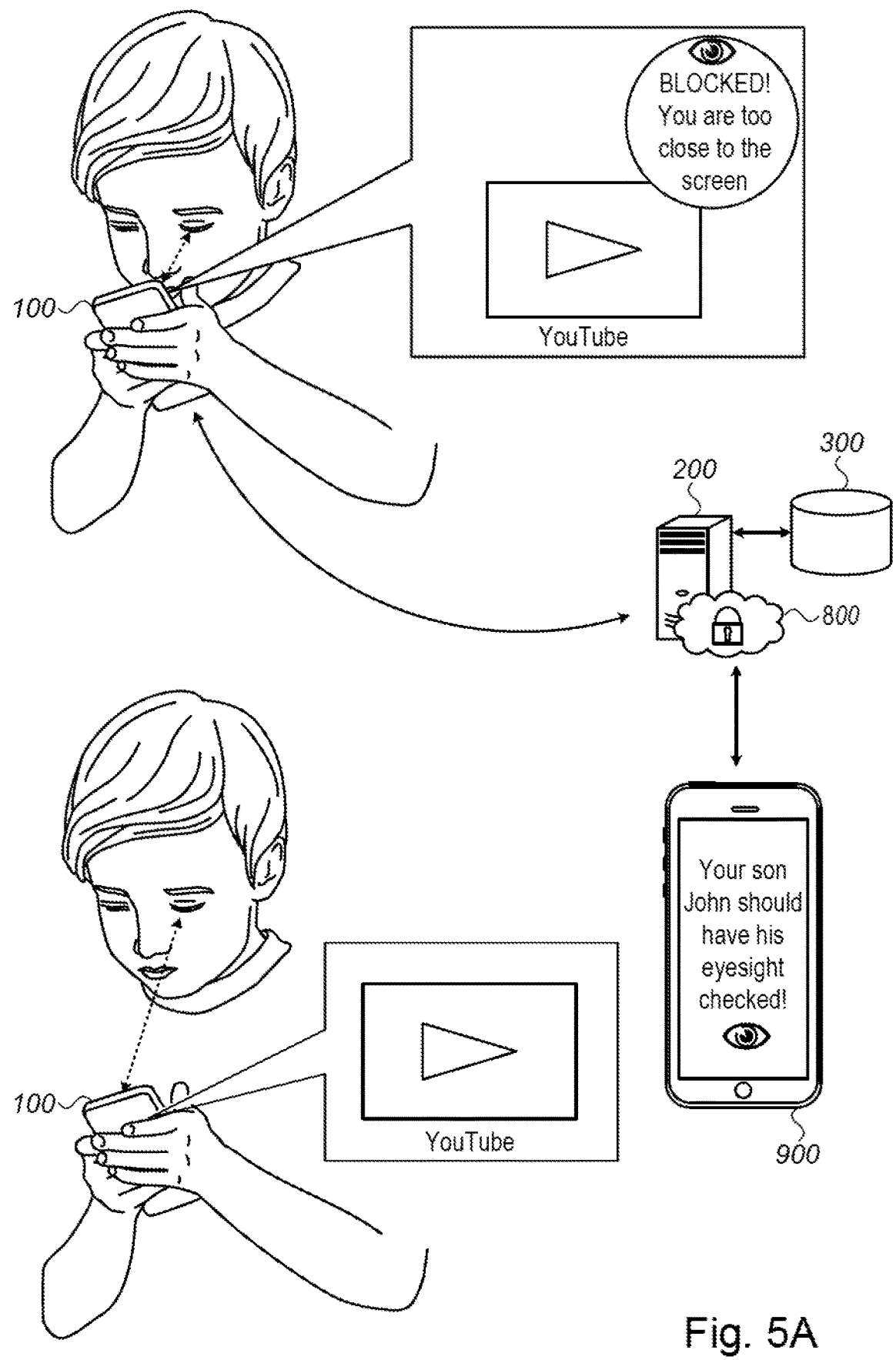
FIGS. 5A and 5B are a schematic flowchart illustrating a method for eye-health monitoring, according to some embodiments of the present invention.
Figure 5B:
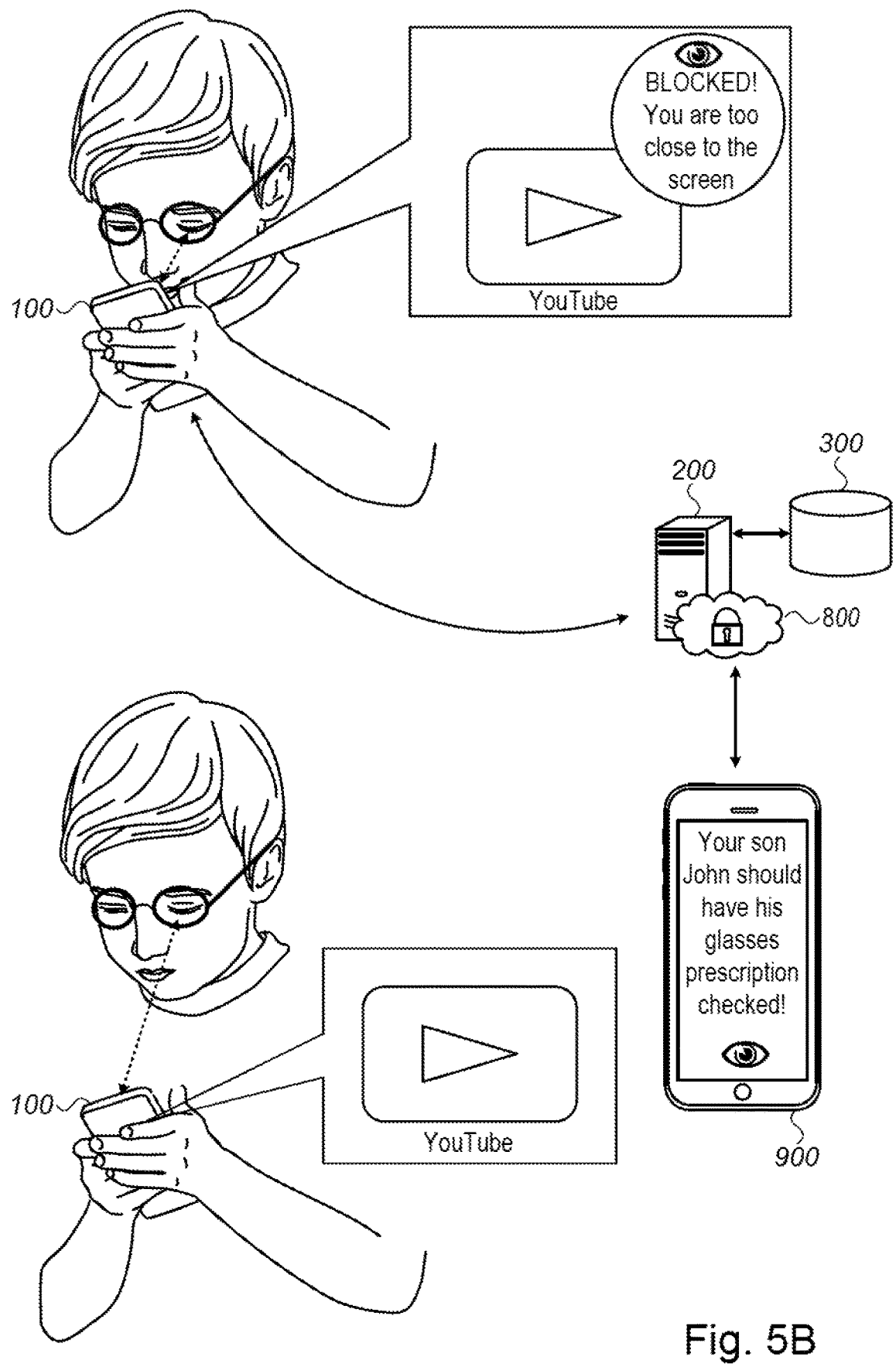

Reference is now made to FIGS. 5A and 5B, which are schematic illustration of a user, without and with glasses, respectively, using device 100. FIG. 5A is an illustration of a user, using device 100 and bringing device 100 closer to his eyes, than a predetermined distance. Once device 100 gets too close to the user's face, glasses and/or eye, crosses a predetermined threshold, as illustrated in FIGS. 5A and 5B, processor 204 generates a notification. in some other embodiments, other monitored conditions relating to the device 100 will be used to adjust the time threshold, distance thresholds associated with the processor 2014 generating a notification. Such conditions may include the ambient light, device position, device location, and device orientation (angle/tilt) relative to the ground and the eyes of the user. For example, the notification can be provided via audio unit 108 and/or display 104, notifying the user that device 100 is too close. For example, as illustrated in FIGS. 5A and 5B, the notification is in the form of a popup message or icon presented on the screen. Such icon would preferably be adjusted to be child friendly and would be designed so as to encourage compliance by the user of the device 100.

FIGS. 5A and 5B, also illustrates that the user used device 100 too close to their face and/ or eye more than a predetermined number of times per session. In this case, processor 204 also generates a notification, for example to supervisor's device 900. Furthermore, processor 204 may also store all the data regarding the event for example on memory 114 and/or database 300. FIGS. 5A and 5B illustrate that after the user moves device 100, further away to a predetermined distance, processor 204, for example via display 104 removes the notification popup.

FIG. 5B also illustrates the difference between a user wearing glasses and a user who is not required to wear glasses. In FIG. 5B the device 100 is also programmed to identify on a continuous basis, if the user of the device 100 is wearing glasses or if the user is not wearing glasses. Such identification can be achieved through the analysis of the images obtained for example through front camera 110. Once the processor 104 identifies that the user is not wearing glasses, it may provide an alert if the user is or is not required to wear glasses during the operation of the device 100. Such alert may be given to the user and/or to a supervisor holding device B 900 through server 200. In some other embodiments of the present invention, if the user is required to wear glasses but only during certain times, the device 100 may provide appropriate alerts to the user, when to wear or remove his glasses. Furthermore, device 100 may provide appropriate alerts to the user, for example to get their prescription upgraded (for example, if the user is wearing glasses but is still holding device 100 to close to their face) or to get their eyes checked for glasses, for example if they are not wearing glasses but holding device 100 to close to their face. The use of the feature described in FIG. 5B may enable better compliance of glasses wearing in children and young adults and will contribute to better eye health in such users.

It should be noted that there may be a variety of different notifications generated by processor 204 depending on the different situations detected by processor 204. Including, but not limited to audio notifications using audio component 108 and/or visual notifications using display 104 unit, for example notifying the user of bad habits such as a holding device 100 in such a manner that may affect a had posture, that the existing glasses need strengthening and/or that glasses are required.

Figure 6A:
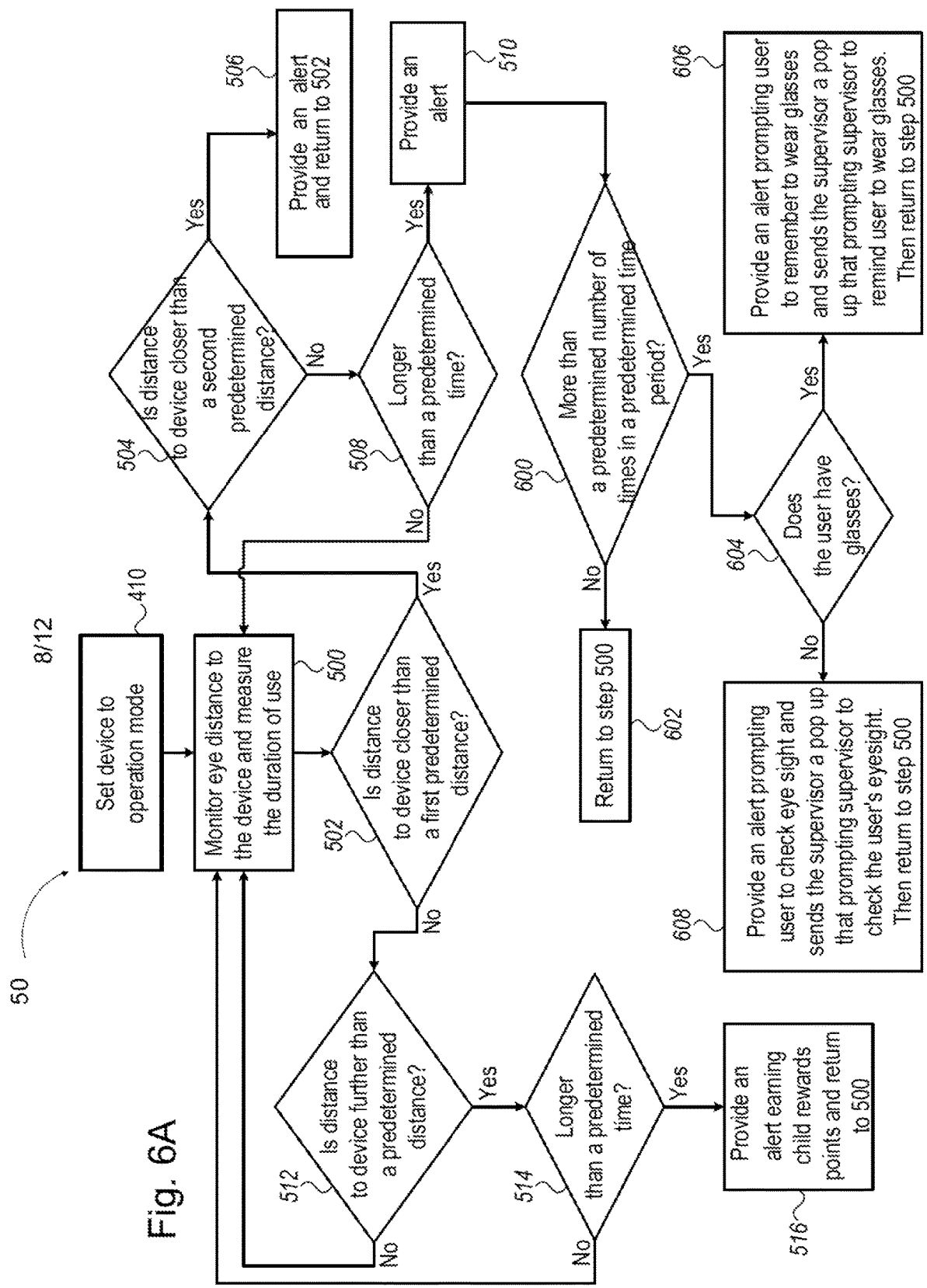
FIGS. 6A and 6B are a schematic illustration of the working environment of a user, with or without glasses, operating a user device and a notification about the user being too close to the screen, according to some embodiments of the present invention.

Turning now to FIG. 6A, which is a flowchart illustration of method 50. Method 50 is executed when the supervisor and/or user selects to set device 100 to "operation mode" and processor 204 starts to analyze information. As indicated in block 500, processor 204 receives data, for example constantly or periodically, for example from camera 110. For example, processor 204 monitors, calculates and/or analyzes the distance between the user's face, glasses and/or eyes to device 100.

At the same time, processor 204, using timer 120, also constantly monitors the duration the user spends in front of device 100 at a certain distance and using an application or any other use of device 100.

As indicated in block 502, processor 204 may determine whether device 100 is held in a distance closer than a predetermined distance. For example, processor 204 continually receives data from device 100 and camera 110 and compares this data with the stored data, for example from database 300, application parameter database 306 and/or memory 114. Based on the comparison, processor 204 may analyze the received data to identify when device 100 is held closer to the user's face and/or eye than a first predetermined distance. As indicated in block 504, processor 204 determines if the distance between device 100 and the user's face/eye is closer than a second predetermined distance. As indicated in block 506, if processor 204 detects that the distance between device 100 and the user's face/eye is closer than a second predetermined distance, processor 204 may generate a notification alert, for example via audio unit 108 and/or display 104. According to the present method, in determining the desired distance between the user and the device 100, the device takes into account the user's details for example as received in step 402 of method 40. In addition, the device 100 can take into account the user's use of glasses and the glasses prescription.

For example, the notification may be in the firm of a pop up block that lets the user know they are too close to device 100. Processor 204 will then return to determining whether device 100 is held in a distance closer than a predetermined distance, as indicated in block 506. As indicated in block 508, if processor 204 determines that the distance between device 100 and the user's face/eye is not closer than the second predetermined distance, but closer than the first predetermined threshold, processor 204 may check whether the duration when device 100 was held closer than the first predetermined distance exceeds a predetermined time frame. As indicated in block 510, processor 204 may generate an alert notification, notifying the user and/or the supervisor, for example via audio unit 108 and/or display 104. For example, in the form of a pop up block that lets the user know they are too close to device 100. If processor 204 determines that the time threshold is not crossed, processor 204 may return to block 500, i.e. monitor the distance and duration of use.

As indicated in block 600, processor 204 checks whether the time threshold is crossed more than a predetermined number of times in a predetermined time session. As indicated in block 604, in case processor 204 determines that the time threshold is crossed more than a predetermined number of times in a predetermined time session, processor 204 checks whether or not the user wears glasses, for example based on data stored in database 300. As indicated in block 606, if processor 204 identifies that the user has glasses, processor 204 may then generate a notification alert. For example, via audio unit 108 and/or display 104. As indicated in blocks 606, processor 204 may also generate a notification to the supervisor's device 900 letting them know of the event, Processor 204 may also suggest ways to operate according to the stored data for example in database 300, memory 114, and/or application parameter 306. For example, as indicated in block 606 processor 204 may suggest that the user should wear their glasses. While device 100 is used, processor 204 may return to block 500, i.e. monitor the distance and duration of use.

As indicated in block 608, if processor 204 identifies that the user does not have glasses, processor 204 may then generate a notification alert to the user or to a supervisor. For example, via audio unit 108 and/or display 104. As indicated in blocks 608, processor 204 may also generate a notification to the supervisor's device 900 letting them know of the event. Processor 204 may also suggest ways to operate according to the stored data for example in database 300, memory 114, and/or application parameter 306. For example, as indicated in block 608 processor 204 may suggest that the user should check their eye-sight. While device 100 is used, processor 204 may return to block 500, i.e. monitor the distance and duration of use.

As indicated in block 600, if processor 204 detects that the time threshold was not crossed more than a predetermined number of times in a predetermined time session processor 204 may return to block 500, i.e. monitor the distance and duration of use, as indicated in block 602.

As indicated in block 512, processor 204 detects whether device 100 is held at the appropriate predetermined distance from the user face and/or eye. If device 100 is held at the appropriate distance, as indicated in block 514, processor 204 determines whether device 100 is held in the appropriate distance longer than a predetermined time. As indicated in block 516, in case device 100 is held in a proper distance longer than the predetermined time, processor 204 may then generate incentive points and/or rewards and send a notification about the incentive points and/or rewards to the user and/or supervisor. Otherwise, processor 204 may return to block 500. For example, the incentive points and/or rewards may be earned as described in the incentive program. As indicated in block 512, if processor 204 determines that the distance between device 100 and the user's face and/or eye is closer that the predetermined distance, processor 204 will return to block 500, i.e. monitor the distance and duration of use.

Figure 6B:
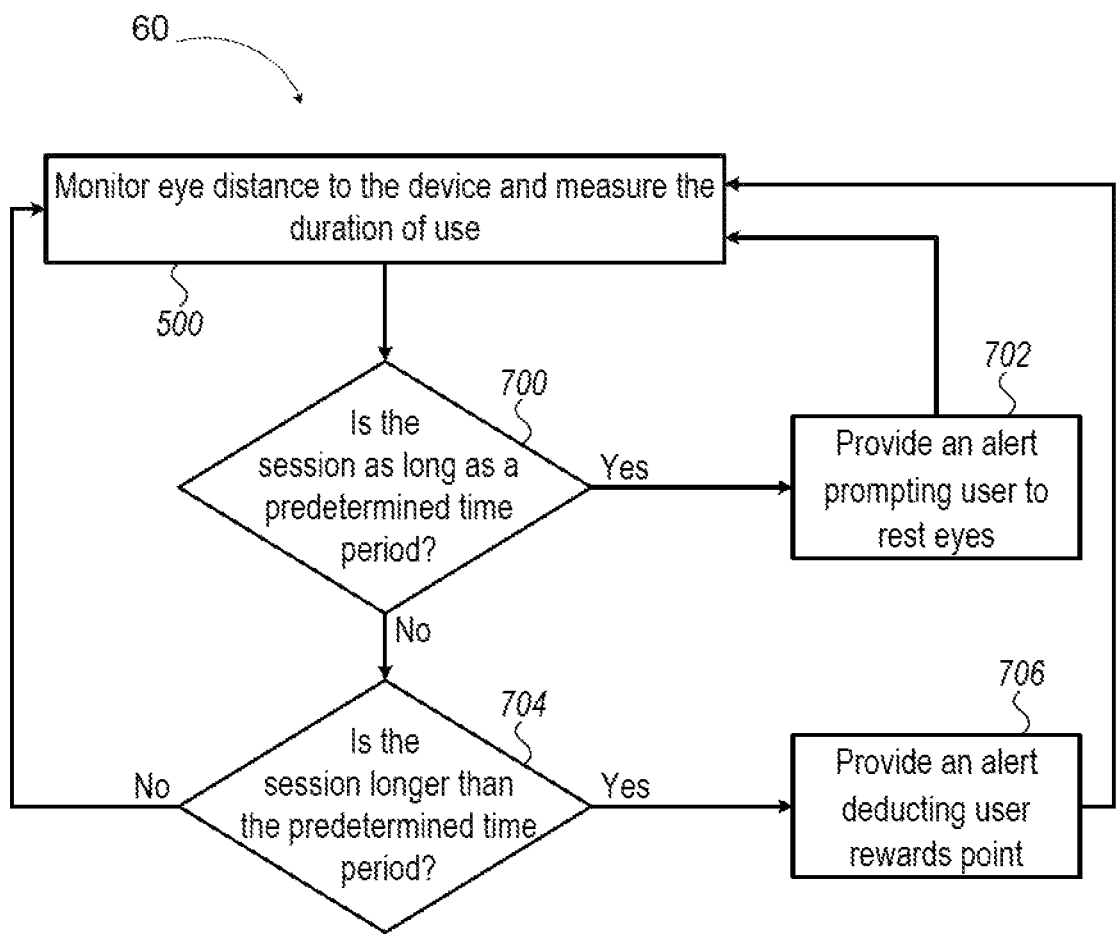

FIG. 6B, which is a flowchart illustration of method 60. The flow chart illustrated in FIG. 6B may start at block 500 described above. Method 60 may run concurrently with method 50. As indicated in block 700, processor 204, using timer 120 may monitor the duration of a working/playing session on device 100. Processor 204 may then check if the session monitored is as long as a predetermined time session. As indicated in block 702, if processor 204 detects that the session is as long as a predetermined time session it may generate a notification, for example via audio unit 108 and/or display 104, notifying the user. As indicated in block 702 the notification may suggest, for example, that the user should rest their eyes. Processor 204 will then return to block 500, i.e. monitor the distance and duration of use. As indicated in block 704, processor 204 detects if the working/playing session monitored by processor 204 is longer than a predetermined time session. As indicated in block 706, processor 204 may generate a notification, notifying the user for example via audio unit 108 and/or display 104. Furthermore, as indicated in block 706 processor 204 may also store the data in database 300 and/or deduct the user incentive points. Processor 204 will then returns to block 500, i.e. monitor the distance and duration of use.

As indicated in block 704, if processor 204 detects that the session is shorter than the predetermined time session, processor 204 will return to block 500, i.e. monitor the distance and duration of use.

In some embodiments of the subject matter, in step 500 of method 50, step 500 method 60 and step 410 of method 70 and at the same time, processor 204 monitors other sensors, such as for example, light sensor 118, also constantly monitors the light environment around the device. For example, if the device is in a well-lit environment, such as outside or inside a building, in a sunny location or in a cloudy environment. The amount of light and the type of light around the device 100 is important for the application to be able to ascertain if the user of the device 100 has been exposed to sunlight which is beneficial to reduce myopia and in addition, to determine if the light emitting from the display 104 with respect to the ambient light at any given time, and in view of the duration the user spends in front of device 100 and/or at a certain distance and/or using an application or any other use of device 100 is likely to increase the occurrence of myopia. In such embodiments, at the same time, processor 204, may also monitor other sensors, such as for example, gyroscope 106, GPS 112, also constantly monitors the location of the device 100 and the deice 100 position. For example, if the device 100 is in motion or not, as well as the device orientation, for example if the device 100 is held in a close to horizontal position. For example, if the device is in movement, such for example in a car or walking, or if the device is in a building or outside a building. Coupled with the other parameters the device is monitoring as provided herein above, including duration the user spends in front of device 100 at a certain distance and using an application or any other use of device 100, alerts may be provided to the user and/or the professional. In such embodiments, an additional step may be taken (not shown) to determine if the environmental conditions surrounding the device 100 require the adjustment of the duration of time the user should use the device 100 without a break and/or the distance the user should maintain.

Figure 6C:
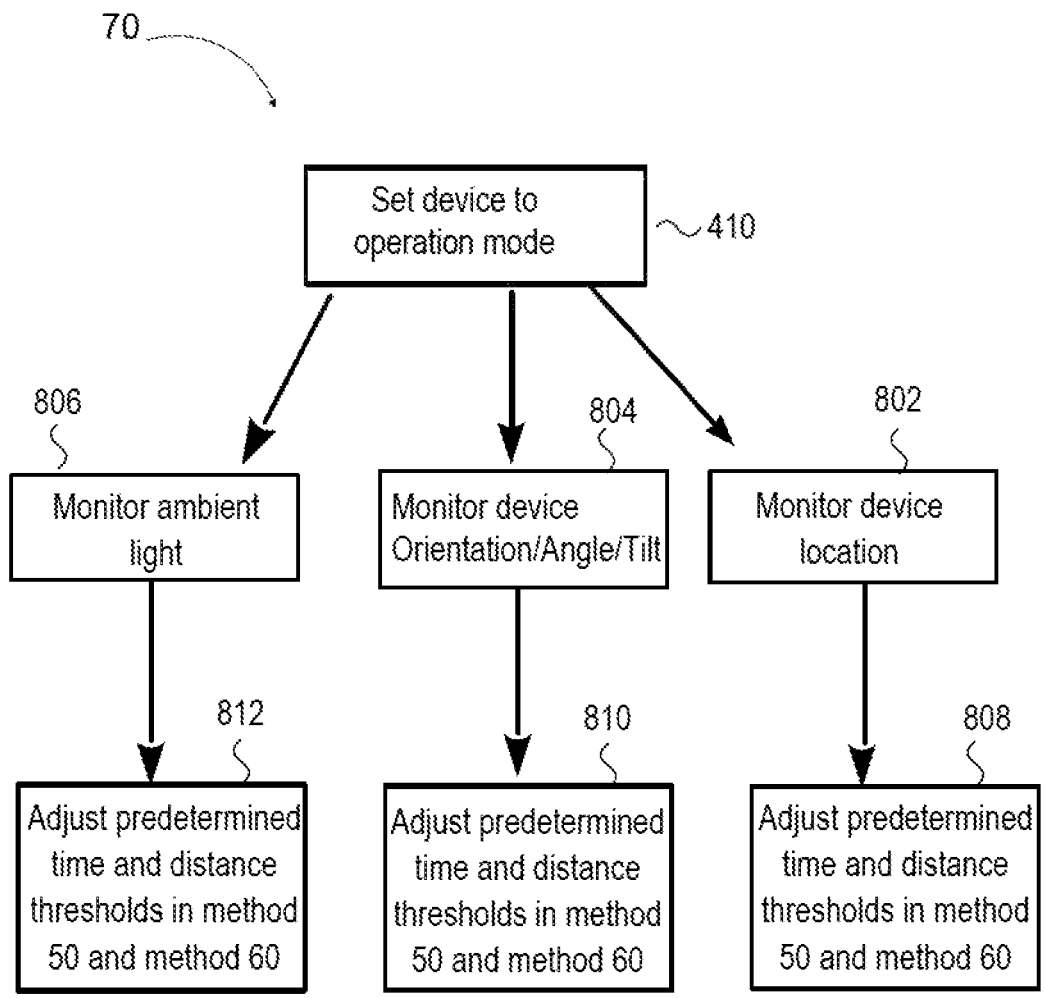

The flow chart illustrated in FIG. 6C may start at block 410, when the device is set is to operation mode. Method 70 may run concurrently or separately with method 50 and with method 60. As indicated in block 802, processor 204, using GPS 112 may monitor the device 100 location. Processor 204 may then check if the location monitored is in the area as predetermined, for example by a supervisor, and may for example adjust the predetermined time session period threshold, for example as shown in method 50 block 508 and/or in method 60 block 700, and/or adjust the predetermined distance threshold, for example as shown in method 50 block 502 and/or in method 60, as indicated in block 808. In accordance with some embodiments, the device 100 location may be inside or outside the home of the user, a predetermined area defined by geospatial coordinates, a predetermined location as determined through the proximity to another device, such as device 100, or a Wi-Fi router, a cellular network tower, or other like device which can indicate the location of the device 100.

As indicated in blocks 804, processor 204, using Gyroscope 106 may monitor the device 100 orientation. Processor 204 may then check if the orientation monitored is aligned with the predetermined orientation and may for example adjust the predetermined time session/period threshold, for example as shown in method 50 block 508 and/or in method 60 block 700, and/or adjust the predetermined distance threshold, for example as shown in method 50 block 502 and/or in method 60, as indicated in block 810. The device 100 orientation refers to the planar position of the device 100, such as for example, how the device 100 is held by the user relative to the ground and relative to the user's head and/or eyes. The orientation may also refer to the angle of the device 100 relative to the eyes of the user or the ground. If the angle of the device 100 screen relative to the eyes of the user is oblique and preferably less than 45 degrees (acute or obtuse), such orientation of device 100 may affect the user's ability to properly view the screen in a clear and easy manner. If the device is held by the user in an orientation which is not suitable for easy viewing of the screen, the processor 204 adjusts the time/distance thresholds to further limit the use of the device in such orientation. The orientation of the device may also refer to the tilt position of the device. Tilt position refers to the change in both angle of the device relative to the ground and the changes in acceleration detected using Gyroscope 106. The processor 204 may check if the device 100 is tilted and calculate the orientation of the device relative to the ground and if the face of the user is identified while the device is tilted, the processor 204 adjusts the time/distance thresholds to further limit the use of the device in such orientation. Just adjustment is appropriate if the child is using the device while walking as it will further strain the eyes of the user and require the user to view the screen at an unsuitable angle while also looking elsewhere and changing the user's focus rapidly. Alternatively, the processor 204 may provide the user with a notification requesting the user change the device 100 orientation to achieve a better orientation to enable easier viewing of the screen of the device.

As indicated in blocks 806, processor 204, using Light sensor 118 may monitor the ambient light around device 100. Processor 204 may then check if the light intensity is in the boundaries of the predetermined light threshold restrictions, and may for example adjust the predetermined time session/period threshold, for example as shown in method 50 block 508 and/or in method 60 block 700, and/or adjust the predetermined distance threshold, for example as shown in method 50 block 502 and/or in method 60, as indicated in block 812. As ambient light changes, the user of the device may require additional effort to use the screen of the device and therefore adjusting the time session/period threshold may assist in reducing the time the user eyes exert effort to use the device 100. Processor 204 process for example the data received from GPS 112, Gyroscope 106, Timer 120 and Light sensor 118 and may then, for example generate an alert, change device 100 display settings, shut off use of device 100 and/or adjust the predetermined time and distance thresholds in method 50 and/or method 60, based on for example the combined data received, supervisors and/or professional instruction and/or the predetermined settings. In some embodiments the processor 204 may provide the user or a supervisor notification if the device is located outside a predetermined location or a predetermined area, is subject to ambient light or when ambient light is no longer detected, when the orientation of the device 100 is outside a predetermined threshold.

Figure 7:
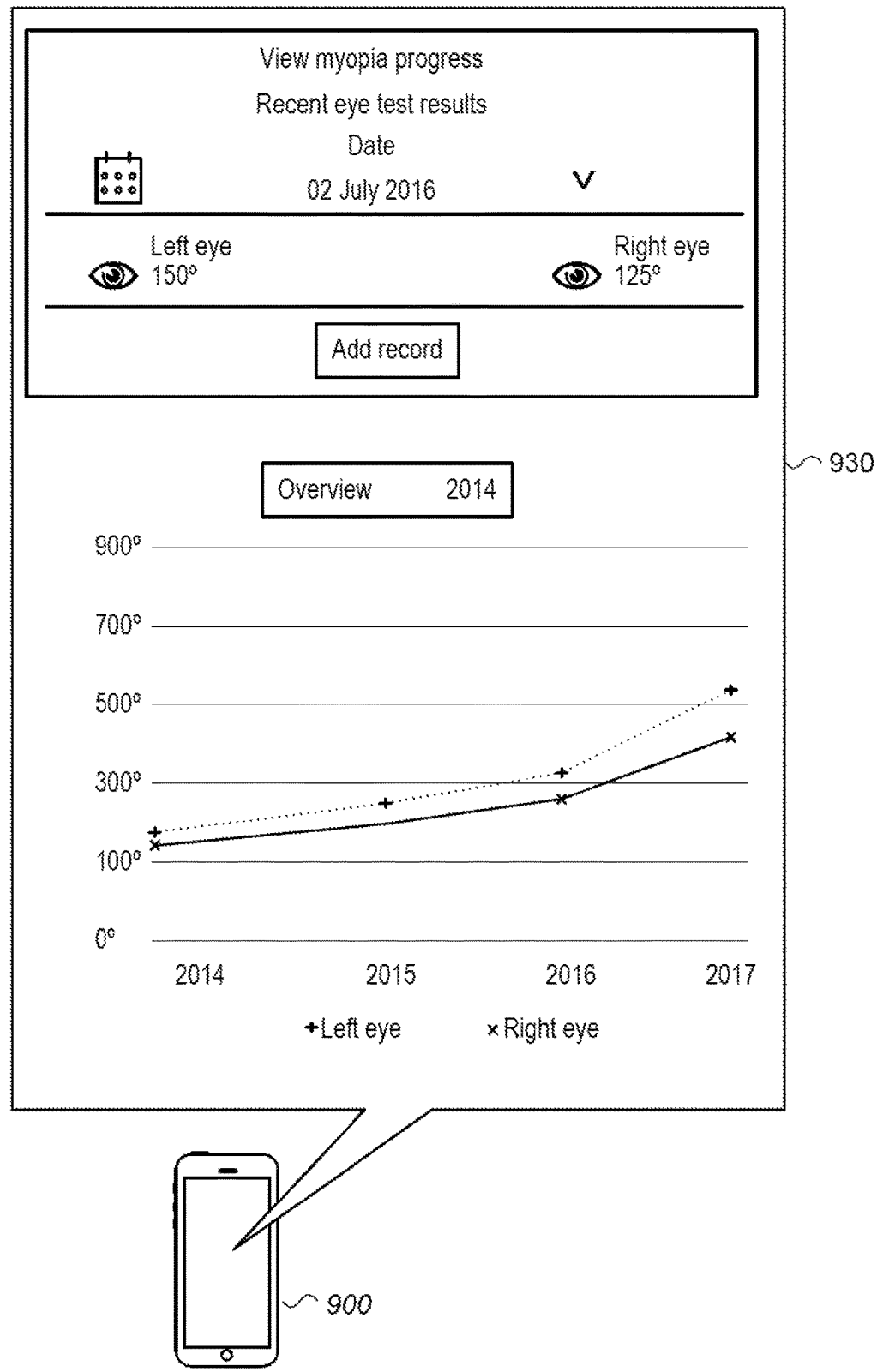
FIG. 7 is a schematic illustration of an exemplary screen viewed on a supervisor's device presenting the user's eye health data along a period of time, according to some embodiments of the present invention.

FIG. 7 is a schematic illustration of a screen 930 shown on supervisor's device 900. Screen 930 may include the user's eye related data accumulated up to a selected or predetermined date. In addition, the eye related date can be presented in various formats. For example, as shown in FIG. 7 in the form of a diagram of the user's eye related data, for example in this illustration it can be seen that the graph depicts the increase of the glasses prescription of the user, for the right eye and for the left eye over the selected time period. Such increase represents a deterioration in the myopic conditions of the user of device 100 as is shown to the supervisor over time. The graphic representation over time of the change in the myopic progress enables the supervisor to closely monitor any changes in the myopic condition of the user which may require the attention of a physician and/or additional corrective measures to prevent the deterioration in the myopic condition of the user.

Figure 8:
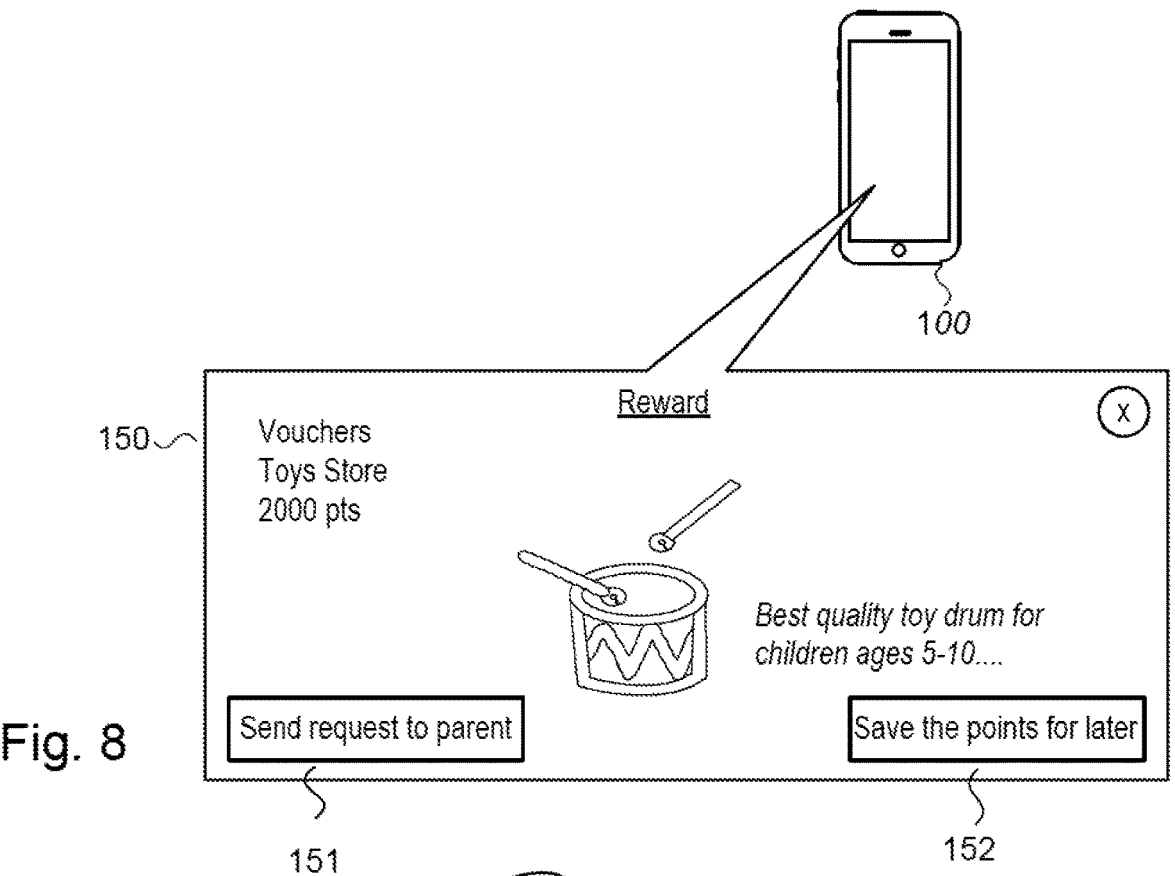
FIG. 8 is a schematic illustration of an exemplary screen viewed on a user's device, notifying the user about earned points, according to some embodiments of the present invention.

FIG. 8 is a schematic illustration of a screen 150 shown on user's device 100, wherein for example the user is rewarded incentive points and earns enough points to trade them into a voucher when the user complies with the alerts issued thereto by the device. In this illustration, for example, when the user is provided an alert in steps 516, 618, 606, 510, 506 of FIG. 6A, 702, 706 of FIG. 6B, and the user complies with the alerts provided, such that the user discontinues use of device 100 and/or maintains the appropriate distance between his eyes and the device 100, the user may be awarded with incentives such as points and/or vouchers and/or rewards. In the present example, the user would receive a notification on device 100 that he received 2,000 points as a reward for complying with. the alerts provided to him, and that these 2,000 points may be redeemed as a voucher to be used in a toy store, for example for the purchase of toy drums. The user can then decide whether to trade the points into a voucher, through pressing a button 151 or save the points for a later use through pressing button 152. For example, for a different voucher or other offerings. It should be noted that the incentive program would motivate the user to correct their behavior in a positive reinforcing manner which is likely to lead to the prevention of deterioration in the myopic condition of the user or even the prevention of myopic problems.

Figure 9:
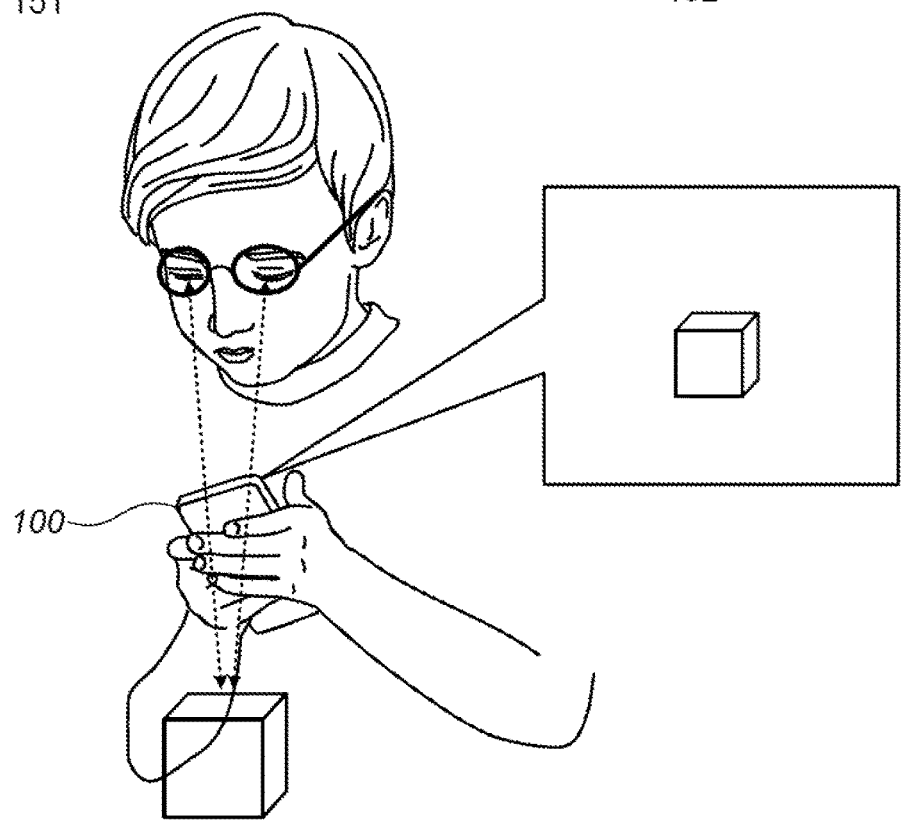
FIG. 9 is a schematic illustration of a user looking at a screen of a user device, having a focus point further away from the actual distance from the user device, according to some embodiments of the present invention.

Turning now to FIG. 9 is an illustration of a user looking at the screen of device 100. In this illustration for example, processor 204 using display 104, presents to the user an image (not shown) or employs a virtual reality application that allows the user to focus his eyes on a focal point distant from the actual focal point of the display 104. For example, the processor 204 may generate result in creating a focal point than the actual distance between device 100 and the user's face and/or eyes. Processor 204 may create for example, a differential depth focus points and/or range while the user is using device 100, according to a predefined focus range and/or time period stored, for example, in memory 114 and/or database 300 as specified by a professional. Changes of the focal point of the user's eyes may be required as pan of the methods of the present subject matter, for example, when the user is not compliant with the alerts provided. For example, when the user is provided an alert in steps 516, 618, 606, 510, 506 of FIG. 6A, 702, 706 of FIG. 6B, and the user fails to comply with the alerts provided, the processor 204 may interrupt the user's use of the device and presents to the user an image or activate a virtual reality application, which requires the user to focus his eyes on a different focal point. This change in the focus range may be used for example as an eye exercises, or as an alternative option for resting the user's eyes, thus preventing or slowing the progression of myopia.

In the context of some embodiments of the present disclosure, by way of example and without limiting, terms such as 'operating' or 'executing' imply also capabilities, such as 'operable' or 'executable', respectively.

Conjugated terms such as, by way of example, 'a thing property' implies a property of the thing, unless otherwise clearly evident from the context thereof.

The terms 'processor' or 'computer', or system thereof, are used herein as ordinary context of the art, such as a general purpose processor, or a portable device such as a smart phone or a tablet computer, or a micro-processor, or a RISC processor, or a DSP, possibly comprising additional elements such as memory or communication ports. Optionally or additionally, the terms 'processor' or 'computer' or derivatives thereof denote an apparatus that is capable of carrying out a provided or an incorporated program and/or is capable of controlling and/or accessing data storage apparatus and/or other apparatus such as input and output ports. The terms 'processor' or 'computer' denote also a plurality of processors or computers connected, and/or linked and/or otherwise communicating, possibly sharing one or more other resources such as a memory.

The terms 'software', 'program', 'software procedure' or 'procedure' or 'software code' or 'code' or 'application' may be used interchangeably according to the context thereof, and denote one or more instructions or directives or electronic circuitry for performing a sequence of operations that generally represent an algorithm and/or other process or method. The program is stored in or on a medium such as RAM, ROM, or disk, or embedded in a circuitry accessible and executable by an apparatus such as a processor or other circuitry. The processor and program may constitute the same apparatus, at least partially, such as an array of electronic gates, such as FPGA or ASIC, designed to perform a programmed sequence of operations, optionally comprising or linked with a processor or other circuitry, The term 'configuring' and/or 'adapting' for an objective, or a variation thereof, implies using at least a software and/or electronic circuit and/or auxiliary apparatus designed and/or implemented and/or operable or operative to achieve the objective.

A device storing and/or comprising a program and/or data constitutes an article of manufacture. Unless otherwise specified, the program and/or data are stored in or on a non-transitory medium.

In case electrical or electronic equipment is disclosed it is assumed that an appropriate power supply is used for the operation thereof.

The flowchart and block diagrams illustrate architecture, functionality or an operation of possible implementations of systems, methods and computer program products according to various embodiments of the present disclosed subject matter. In this regard, each block in the flowchart or block diagrams may represent a module, segment, or portion of program code, which comprises one or more executable instructions for implementing the specified logical function(s). It should also be noted that, in some alternative implementations, illustrated or described operations may occur in a different order or in combination or as concurrent operations instead of sequential operations, to achieve the same or equivalent effect.

The corresponding structures, materials, acts, and equivalents of all means or step plus function elements in the claims below are intended to include any structure, material, or act for performing the function in combination with other claimed elements as specifically claimed. As used herein, the singular forms "a", an and "the" are intended to include the plural forms as well, unless the context clearly indicates otherwise. It will be further understood that the terms "comprising", "including" and/or "having" and other conjugations of these terms, when used in this specification, specify the presence of stated features, integers, steps, operations, elements, and/or components, but do not preclude the presence or addition of one or more other features, integers, steps, operations, elements, components, and/or groups thereof.

The terminology used herein should not be understood as limiting, unless otherwise specified, and is for the purpose of describing particular embodiments only and is not intended to be limiting of the disclosed subject matter. While certain embodiments of the disclosed subject matter have been illustrated and described, it will be clear that the disclosure is not limited to the embodiments described herein. Numerous modifications, changes, variations, substitutions and equivalents are not precluded.

The invention claimed is:

1. A method of controlling an application for monitoring eye health of a user of a device, the method comprising:
installing on a user device an application for supervised use of the user device;
installing on a supervisor device an application for supervising use of the user device;
providing a computerized server configured to serve as an intermediate between the user device and the supervisor device:
receiving, at the server, information from the user device and from the supervisor device, said information comprising user information related to the user normally wearing glasses or normally not wearing glasses;
analyzing the information by the server;
adding the information to a user profile;
storing the information in a database;
generating notifications for the user device and the supervisor device responsive to analyzing the information by the server;
wherein the supervisor device is configured to provide configuration information for the user device; and
wherein the user device is configured to perform:
receiving an indication that an event occurred associated with use of the user device;
transmitting information related to the event to the server;
updating information on the user device according to the configuration information provided by the supervisor device;
generating a personalized user interface and enabling display of the interlace on the user device;
detecting a distance of an eye or of the user from the user device; and
providing an indication once the distance exceeds a predefined distance threshold for a predefined time period, wherein the predefined distance threshold is adjusted based on monitored user device orientation,
wherein when a distance threshold is exceeded more than a predetermined number of times in a predetermined time session,
determining if the user is currently wearing glasses;
when determining the user is currently wearing glasses, and determining according to the user profile that the user normally wears glasses, generating an indication on the supervisor device to check user's eye-sight;
when determining the user is currently not wearing glasses, and determining according to the user profile that the user normally wears glasses, generating an indication on the user device and on the supervisor device that the user is to wear the glasses;
and when determining that the user is currently not wearing glasses, and determining according to the user profile that the user normally does not wear glasses, generating an indication on the supervisor device to check user's eye-sight.

2. The method according to claim 1, further comprising detecting glasses of the user and monitoring the distance between the user's glasses and the user device.

3. The method according to claim 1, further comprising detecting the location of the user device and monitoring the distance between the user's face and the user device or the duration of the use of the user device, based on the location of the user device.

4. The method according to claim 1, further comprising detecting the ambient light around the user device and monitoring the distance between the user's face and the user device or the duration of the use of the user device, based on the amount of light surrounding the user device.

5. The method according to claim 1, further comprising receiving information at the user device from the supervisor device.

6. The method according to claim 1, further comprising generating a varying user interface, and providing the user the effect of focusing on objects located in a variety of different distances.

7. The method according to claim 1, further comprising generating a varying user interface upon failure of the user to comply with the indication, and providing the user the effect of focusing on objects located in a variety of different distances.

8. The method according to claim 1, further comprising generating according to received information from the user device, the server or from the supervisor device alerts about one or more of the options selected from a group consisting of the user's eyes condition, the user's use of the user device, the ambient light surrounding the user device, the location of the user device and the progression of myopic condition of the user of the user device.

9. The method according to claim 1, further comprising providing the user of the user device an incentive if the indication is complied with.

10. The method according to claim 4, further comprising receiving from the user device information about detected ambient light, and instructing the user device to apply a blue light filter once the ambient light/screen light differential meets a pre-determined threshold.

11. The method according to claim 1, further comprising receiving from the user device information about a detected orientation of the device and instructing the user device to notify the user when the holding position exceeds a predetermined threshold.

12. The method according to claim 1, further comprising adjusting the predefined distance threshold based on information received from sensors installed in the user device.

13. The method according to claim 1, comprising adjusting the predefined time period based on information received from sensors installed in the user device.

14. The method according to claim 1, further comprising presenting to the user an image that allows the user to focus his eyes on a focal point distant from the actual focal point of a display of the user device.

15. A system for controlling an application for monitoring the eye health of a user, comprising:
- a user device with an application installed for supervised use of the user device;
- a supervisor device with an application installed for supervising use of the user device;
- a computerized server configured to serve as an intermediate between the user device and the supervisor device;
- wherein the server is configured to perform the following:
  - receiving, at the server, information from the user device and from the supervisor device, said information comprising user information related to the user normally wearing glasses or normally not wearing glasses;
  - analyzing the information by the server;
  - adding the information to a user profile;
  - storing the information in a database;
  - generating notifications for the user device and the supervisor device responsive to analyzing the information by the server;
- wherein the supervisor device is configured to provide configuration information for the user device; and
- wherein the user device includes a memory for storing code instructions, a hardware processor and a display, the hardware processor is configured to execute an application for supervised use of the user device with code instructions for:
  - receiving indication that an event occurred that is associated with use of the user device;
  - transmitting information related to the event to the server;
  - updating information on the user device according to the configuration information provided by the supervisor device;
  - generating a personalized user interface and enabling display of the interface on the display of the user device;
  - detecting a distance of an eye of the user from the user device; and
  - providing an indication once the distance between the user and the device exceeds a predefined distance threshold for a predefined time period, wherein the predefined distance threshold is adjusted based on monitored user device orientation,
- wherein when a distance threshold is exceeded more than a predetermined number of times in a predetermined time session,
- determining if the user is currently wearing glasses;
- when determining the user is currently wearing glasses, and determining according to the user profile that the user normally wears glasses, generating an indication on the supervisor device to check user's eyesight;
- when determining the user is currently not wearing glasses, and determining according to the user profile that the user normally wears glasses, generating an indication on the user device and on the supervisor device that the user is to wear the glasses;
- and when determining that the user is currently not wearing glasses, and deteimining according to the user profile that the user normally does not wear glasses, generating an indication on the supervisor device to check user's eye-sight.

\* \* \* \* \*